(12) United States Patent
Brennen (10) Patent No.: US 6,520,916 B1
(45) Date of Patent: Feb. 18, 2003

(54) ULTRASOUND IMAGING SYSTEM AND METHOD FOR IMPLANTABLE AND INVASIVE DEVICES

(75) Inventor: Kenneth R. Brennen, Fridley, MN (US)

(73) Assignee: Medtronic, Inc., Minneapolis, MN (US)

( * ) Notice: Subject to any disclaimer, the term of this patent is extended or adjusted under 35 U.S.C. 154(b) by 155 days.

(21) Appl. No.: 09/631,136

(22) Filed: Aug. 2, 2000

(51) Int. Cl.$^7$ .................................................. A61B 8/14
(52) U.S. Cl. ........................................ 600/463; 600/466
(58) Field of Search .................................. 600/407, 437, 600/443, 449, 450, 453–457, 459–468, 481; 607/116, 119, 122; 604/95, 96, 281, 282; 310/328, 331, 358, 359, 323, 366

(56) References Cited

U.S. PATENT DOCUMENTS

| | | |
|---|---|---|
| 4,697,595 A | 10/1987 | Breyer et al. |
| 5,114,414 A | 5/1992 | Buchbinder |
| 5,161,536 A | 11/1992 | Vilkomerson et al. |
| 5,315,205 A | 5/1994 | Ohno et al. |
| 5,318,525 A | 6/1994 | West et al. |
| 5,343,865 A | 9/1994 | Gardineer et al. |
| 5,421,336 A | 6/1995 | De Bernardis |
| 5,728,124 A | 3/1998 | Cockburn et al. |
| 5,968,085 A | 10/1999 | Morris et al. |

*Primary Examiner*—Marvin M. Lateef
*Assistant Examiner*—Ali M. Imam
(74) *Attorney, Agent, or Firm*—Girma Wolde-Michael; Michael C. Soldner (57) ABSTRACT

An improved system and method to provide visualization of implantable leads, catheters, or other implantable devices is disclosed. According to the invention, an unmodified guiding device such as a stylet or guidewire is frictionally coupled to a vibration device. This guiding device is further inserted into the device to be visualized. When activated, the vibration device transfers longitudinal waves to the guiding device, which, in turn, transfers the waves to the device that is to be visualized. These waves are detected by an imaging device, which then generates a Doppler image of the implantable device. According to one aspect of the invention, the vibration device includes a piezoelectric actuator. According to another aspect of the invention, the frequency of the waves that are transferred by the vibration device is selectable.

40 Claims, 5 Drawing Sheets

FIG. 7

ULTRASOUND IMAGING SYSTEM AND METHOD FOR IMPLANTABLE AND INVASIVE DEVICES

BACKGROUND OF THE INVENTION

The present invention relates to visualization of medical devices within a body generally and, more particularly, to visualization by means of ultrasound imaging of implantable cardiac pacing or defibrillation leads equipped with guiding stylets, guidewires, needles, or other guiding devices.

Cardiac pacing and defibrillation leads are generally placed under fluoroscopic observation, allowing the physician to follow the lead as it is passed through the venous system into the heart. However, as fluoroscopes are extremely expensive, a less costly method of visualization of cardiac pacing and defibrillation leads would be desirable. Additionally, it would be advantageous to use the guiding mechanisms as delivered without modification of any sort. One alternative mechanism for visualization of pacing leads placed within the body involves the use of an ultrasonic transducer located in the distal end of a stylet that is coupled to a vibrator connected to the proximal end of the stylet. In U.S. Pat. No. 5,968,085 issued to Morris and Lipson, incorporated herein by reference in its entirety, the use of an ultrasonic transducer coupled to a stylet or guidewire to facilitate the display of the lead position within the body on external ultrasound equipment is disclosed. Other examples of such visualization and localization systems are disclosed in U.S. Pat. No. 5,421,336 issued to DeBernardis, U.S. Pat. No. 5,161,536 issued to Vilkomerson et al, and in U.S. Pat. No. 4,697,595 issued to Breyer et al., all incorporated herein by reference in their entireties. In particular, U.S. Pat. No. 5,343,865 to Gardineer et al. discloses a system that uses a rigid coupling mechanism to transfer vibrations to a needle or cannula. The vibrations may be transferred in the X, Y, and Z planes.

One problem with transferring vibrations to a longer, flexible structure such as a lead body involves the difficulty in transferring vibrations around bends in the leads occurring during lead placement within the venous system. In practice, it has been found that transverse waves applied to a stylet inserted into a pacing lead are generally not transmitted around the bends typical of a lead used in clinical practice. In the region of a bend, the stylet is forced against the wall of the lead lumen. Friction with the lead wall dampens the vibrations so that a color Doppler image cannot be obtained beyond the bend. Similarly, pinching the lead eliminates the Doppler image beyond the pinch point.

What is needed, therefore, is an improved system that can be adapted for transferring vibrations down an elongated, flexible structure such as a lead body so that a color Doppler image can be generated to indicate lead location.

SUMMARY OF THE INVENTION

The present invention is directed to an improved visualization of cardiac pacing or defibrillation leads used in conjunction with an unmodified stylet or guidewire that is inserted through a vibrator. This present invention accomplishes this enhancement by means of a piezoelectric activator by which the user can vary the sweep frequency of the vibration to enhance the visualization of various portions of the lead (e.g., the lead tip as well as the fixation tines) on a color Doppler ultrasound system. This invention enhances the Doppler images of pacemaker and defibrillator leads and catheters that are equipped with guidewires, stylets, or needles, and provides images that cannot normally be visualized via conventional ultrasound equipment. The piezoelectric activator produces linear, i.e., longitudinal, vibrations throughout the stylet, that are then transferred to the pacing lead. These vibrations enhance the Doppler image of the whole lead or catheter as well as the lead tip, which cannot normally be imaged via conventional ultrasound equipment. A stylet is advanced through the piezoelectric activator via a modified stylet guide, through a curved piece of hypodermic tubing (hypo tube) coupled to a vibrating diaphragm, then through a standard stylet guide, and into the proximal entry orifice of the lead connector pin. When the vibrating diaphragm is driven by an oscillatory signal, the hypo tube rubs against the stylet thereby transferring the vibration to the stylet. When united to the lead or catheter, the stylet may be used in the conventional manner to assist passage of the lead or catheter through the venous system to gain access to the superior vena cava and, from there, to the chamber(s) of the heart. Throughout this passage, the operator may apply varying vibration frequencies to the stylet to allow visualization of the lead or catheter position at various critical points.

The present invention is adapted to allow longitudinal waves to be transferred along the length of the stylet without being dampened by friction between the stylet and the lead lumen. Friction between the curved hypo tube and the stylet transfers energy from the vibrating diaphragm to the stylet. Because the stylet is an incompressible body, longitudinal vibrations introduced at the proximal end of the stylet are transmitted to the distal end of the stylet. Friction between the stylet and the lead lumen wall transfers some of the vibrational energy to the lead body wherever the stylet makes contact with the lead body. As a result, waves may be transferred around bends and kinks in the lead. A component of this energy is converted to radial vibrations that make the entire course of the lead body visible on Doppler ultrasound.

The current invention is adapted for use with any ordinary, unmodified, stylet or other guiding device. For example, the stylet insertion pin is anchored to the vibrating diaphragm via a friction fit provided by the curved hypo tube. The hypo tube thereby acts as a short extension of the lead or catheter, and freely admits any conventional stylet, guidewire, or other guiding device acceptable for use with the selected lead. The tubing that transfers vibrational energy to the stylet is sized to allow a sliding fit for any stylet that may be used with a selected lead. The dynamic performance of the stylet as used in conjunction with the current invention is not significantly different from the performance of the stylet as used without the inventive system. Moreover, because the stylet is not an integral part of the vibrating mechanism, any disposable stylet may be employed with the system, whereas the remainder of the system is not disposable.

DETAILED DESCRIPTION

Figure 1:
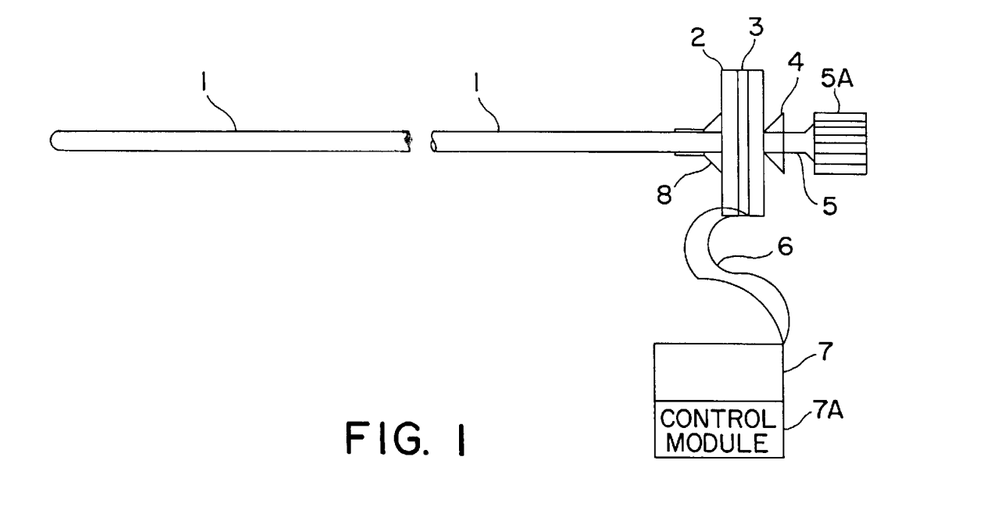
FIG. 1 is a plan view of a stylet coupled to a piezoelectric activator, employed to assist in visualizing the location of the lead of FIG. 2.
Figure 2:
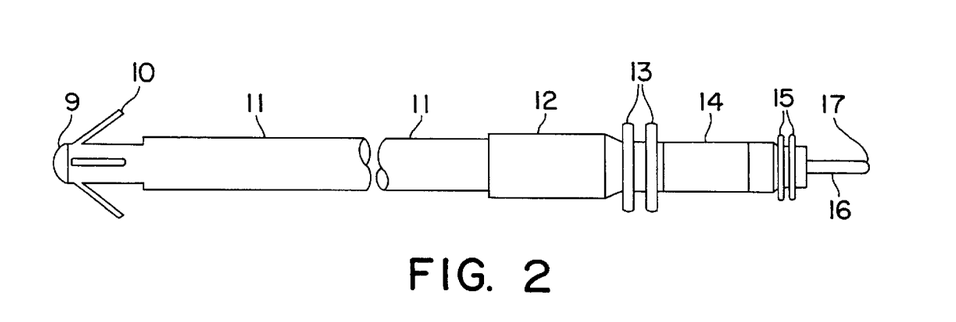
FIG. 2 is a plan view of a lead in which the present invention is practiced in conjunction with a vibrating stylet or guidewire.

FIG. 1 is a plan view of a stylet 5, corresponding to the stylet inserted in the lead in FIG. 2, in conjunction with a piezoelectric activator 2. Knob 5A is visible at the proximal end of the stylet. The stylet 5 is passed through a modified stylet introducer 4, through a hypo tube (see FIG. 4) coupled to the vibrating diaphragm 3. This coupling can be performed by bonding the tube to the diaphragm using an adhesive such as a silicon adhesive. Other types of coupling mechanism could be utilized. For example, the tube could be maintained in position using the passive tension of the slightly compressed tube walls as exerted against the diaphragm. The distal end of the stylet 5 is introduced into the proximal end of the lead connector pin via the unmodified stylet introducer 8 that is bonded to the piezoelectric activator 2. The piezoelectric activator 2 is coupled to a source of ultrasound energy 7 via transmission wires 6. The piezoelectric activator 2 may correspond to that disclosed in U.S. Pat. No. 5,315,205 to Ohno et al. The source of ultrasound energy 7 may correspond to that disclosed in U.S. Pat. No. 5,343,865 issued to Gardineer et al. and incorporated herein by reference in its entirety. This energy source may include a control module 7A to allow the frequency of the supplied energy to be controlled.

When activated, the piezoelectric activator 2 causes the stylet to vibrate longitudinally. The acoustic vibrations that propagate down stylet 5 are transferred to the pacing lead which becomes illuminated in an ultrasound display through which the stylet and lead pass, thereby enhancing the Doppler image of the lead and lead tip. The piezoelectric activator 2 may also be used to vibrate a guidewire, as discussed below.

Although FIG. 1 illustrates the use of the current invention using a lead, the current invention is likewise adaptable for use with a steerable catheter of the type having a lumen to receive a guidewire. Examples of such catheters are shown and described in U.S. Pat. Nos. 5,318,525 and 5,114,414 assigned to the assignee of the current invention, and which are incorporated herein by reference in entirety. The invention is likewise suitable for use with other similar implantable devices.

FIG. 2 is a plan view illustrating the general configuration of a cardiac pacing lead according to the present invention. The lead is provided with a pacing electrode 9 at its distal tip, and associated tines 10 that assist in maintaining the lead in its desired position within the heart. Electrode 9 and tines 10 are mounted at the distal portion of an elongated insulative lead body 11 that terminates at its proximal end in an electrical connector assembly 12. Connector assembly 12 carries a connector pin 16 and a connector ring 14 in conjunction with sealing rings 13 and 15. Connector assembly 12 as illustrated corresponds to an IS-1 standard electrical connector. In the embodiment illustrated, connector pin 16 is coupled to electrode 9, while connector ring 14 is unused. In other embodiments, connector ring 14 might be coupled to an additional cardiac pacing electrode, a defibrillation electrode, or a sensor. Emerging from connector pin 16 is the knob 5A of a stylet inserted through connector pin tip 17, used to advance the lead to its desired location within the heart in a conventional manner. The structure of the lead as illustrated corresponds to a conventional cardiac pacing or defibrillation electrode.

Figure 3:
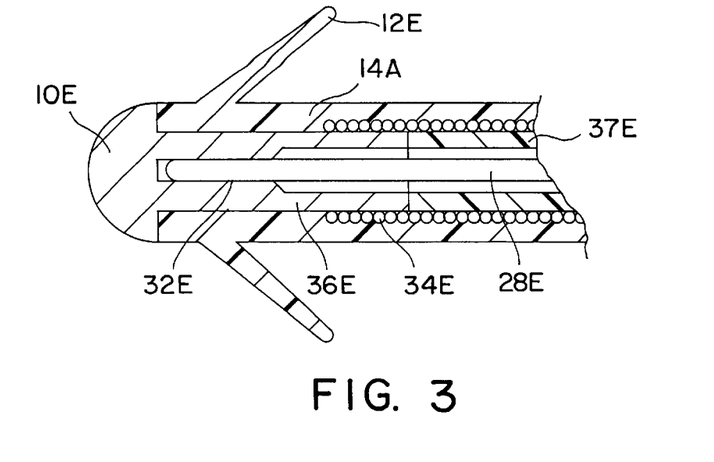
FIG. 3 is a cross-sectional view through the distal portion of a typical pacing lead used in the present invention that employ a vibrating stylet.

FIG. 3 is a sectional view through the distal portion of a typical pacing lead used in the present invention. An electrode 10E is mounted to the distal end of the insulated lead body 14A, which also carries pliant times 12E. The distal portion of 10E is provided with a reduced diameter bore 32E which mechanically engages the distal end of stylet 28E, coupling them together so that the vibrations of the stylet 28E are coupled to the surrounding body fluid via the electrode 10E. The distal tip of stylet 28E may bear against the interior of electrode 10E and may be employed to advance the lead through the vascular system. Electrode shank 36E is coupled to a connector pin at the proximal end of the lead by means of coiled conductor 34E that may be welded or otherwise attached to electrode shank 36E. An optional insulative sleeve 37E is provided internal to conductor 34E.

Figure 4:
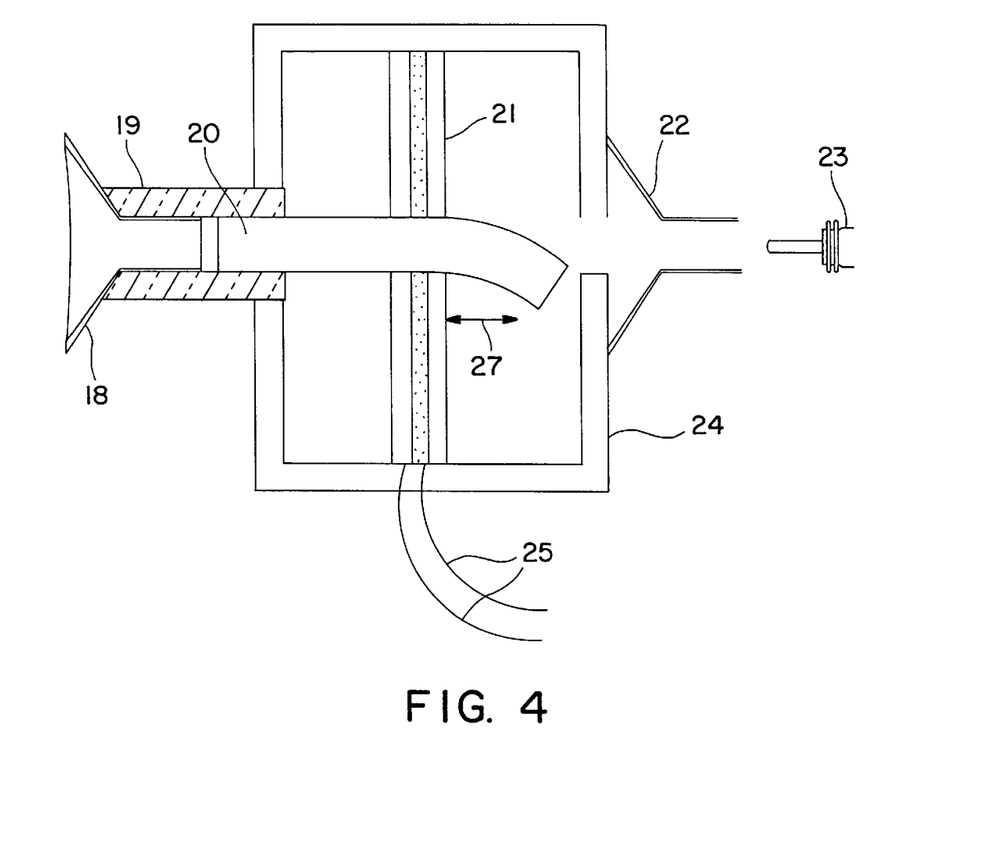
FIG. 4 is a cross-section lateral view of the present invention through which the stylet or guidewire is passed and then inserted into a pacing lead.

FIG. 4 is a plan view (lateral) of the present invention through which the distal end of a stylet is inserted through a modified stylet guide 18, then through a piece of curved hypodermic tubing (hypo tube) 20, out through a second stylet guide 22, and into an orifice located in the distal end of a pacing lead 23. The modified stylet guide 18 is stabilized to the housing 24 of the piezoelectric activator via a silicone-bonding agent 19 or any other type of suitable bonding agent. Vibrating diaphragm 21 is coupled to housing 24 via a bonding adhesive, via grooves in the diaphragm housing, or via some other coupling mechanism. Signals of varying frequency are transmitted via the signal input wires 25 to the diaphragm 21, causing it to vibrate longitudinally, as shown by arrow 27. Control of signal frequency may be provided by control module 7A (FIG. 1.) The longitudinal vibrations are transferred to hypo tube 20, which then transfers the vibrations to the stylet through friction. It may be noted that the inner surface of the hypo tube 20 is able to remain in contact with the stylet because of the curvature of hypo tube.

In FIG. 4, proximal end of hypo tube 20 is shown to contact silicone bonding agent. In this configuration, hypo tube slidably engages the bonding agent so that the portion of the hypo tube contacting the silicone bonding agent is able to vibrate longitudinally. In an alternative embodiment shown in FIG. 5, the entire length of the hypo tube is contained within diaphragm housing 26.

Figure 5:
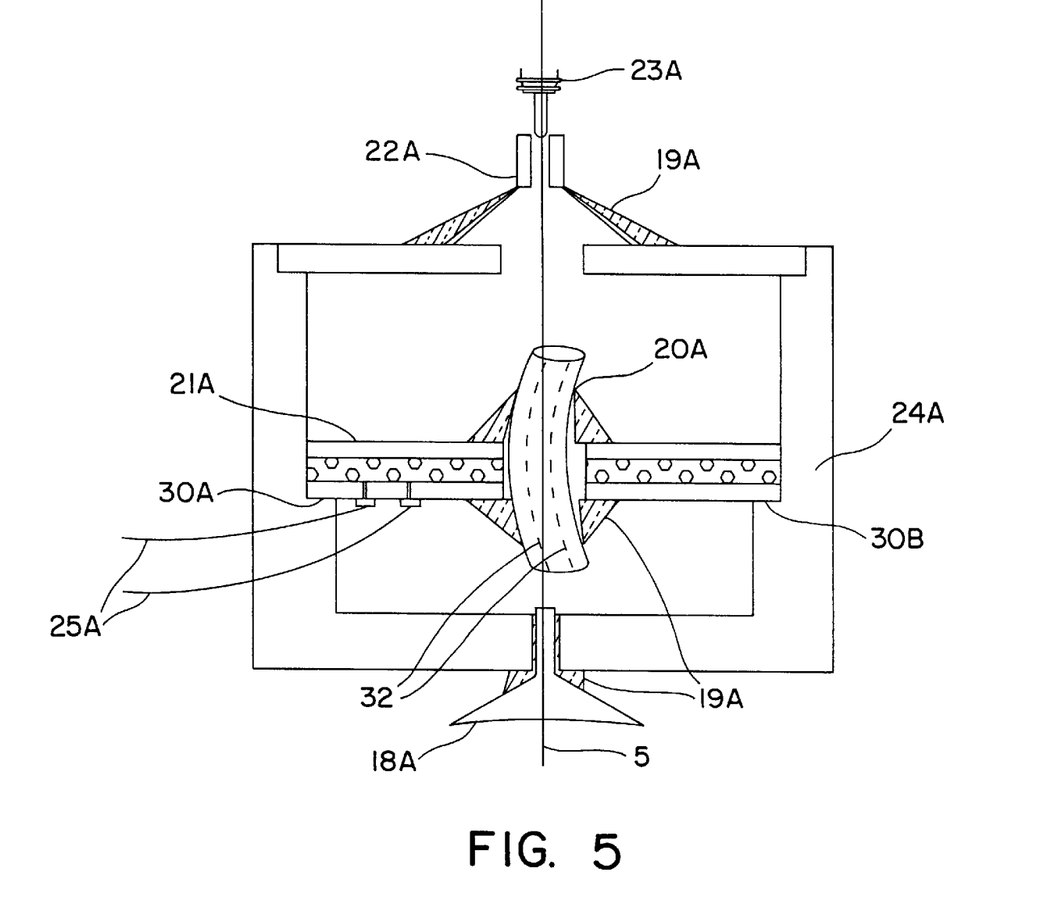
FIG. 5 is a cross-section superior view of the present invention illustrating the curved hypo tube in intimate contact with the vibrating diaphragm of the piezoelectric activator.

FIG. 5 is a plan view (superior) of the present invention that highlights the curvature of the hypo tube 20A. In this embodiment, diaphragm 21A is maintained in contact with shoulders 30A and 30B of diaphragm housing 24A. This view further shows an embodiment wherein hypo tube is entirely contained within diaphragm housing 24A. This embodiment has the advantage of providing two curved ends of hypo tube 20A for contacting stylet 5. As noted above, the curvature of the hypo tube allows the stylet 5 to remain in intimate contact with at least one of the hypo tube's inner surfaces 32 (shown dashed) at all times. Such contact allows the transfer via friction of longitudinal signals of varying frequency to the stylet. These signals are, in turn, frictionally transferred to the lead itself. This acoustic signature obviates the need for a transducer located in the stylet, as well as the need for specialized pacing leads to accommodate such a stylet, guidewire, or lead.

As noted above, because the hypo tube is frictionally coupled to the stylet or guidewire 5, almost any size and model guidewire may be utilized. Furthermore, the coupling mechanism allows the stylet to be readily disposable. Finally, it has been shown that the frictional coupling mechanism used by the present invention to transfer longitudinal waveforms from the diaphragm to the guiding device performs in a superior manner as compared to prior art designs that utilize non-frictional coupling to achieve this transfer. This is because the sliding motion of the hypo tube against the guiding device provides a very efficient energy transfer mechanism.

Figure 6A:
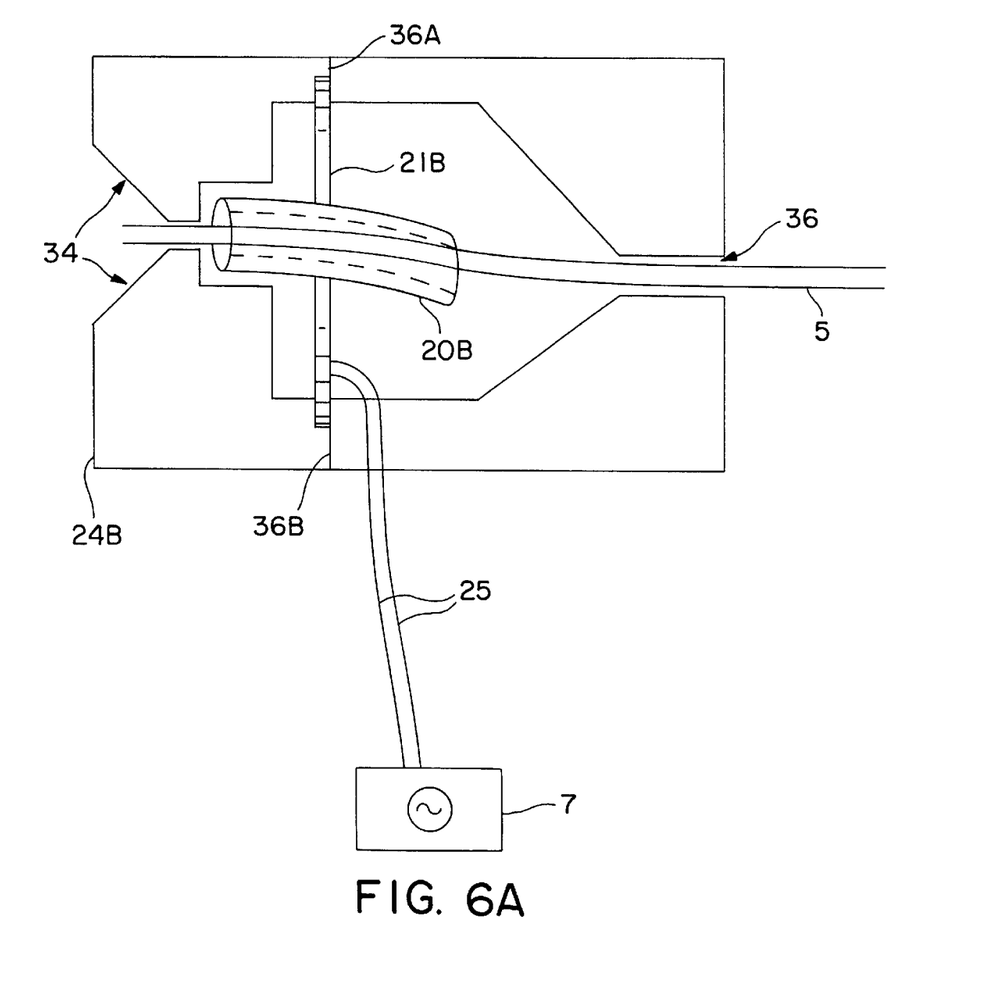
FIG. 6A is a plan view of an alternative embodiment of the present invention.

FIG. 6A is a plan view of an alternative embodiment of the present invention. In this embodiment, housing 24B is integrally formed with a first and second stylet guide 34 and 36, respectively. For example, housing 24B could be formed of first and second molded plastic components coupled along seams 36A and 36B. Diaphragm 21B is seated within molded grooves formed within housing 24B. The diaphragm may be further secured to housing using any type of adhesive material such as a silicon-bonding agent.

Figure 6B:
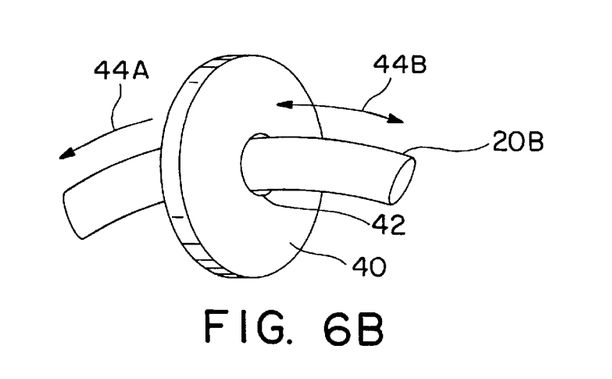
FIG. 6B is a perspective view of one embodiment of a diaphragm employed by the current invention.

FIG. 6B is a perspective view of one embodiment of a diaphragm employed by the current invention. This view is shown and described by referencing the elements of FIG. 6A, but it will be understood that this embodiment could be included within the systems shown in FIGS. 4 and 5 as well. In this embodiment, the diaphragm 21B is a piezoelectric disk 40 such as a unimorph. The piezoelectric disk 40 includes an aperture 42 through which a curved hypo tube 20B is positioned. When activated, the piezoelectric disk vibrates along the longitudinal axis of hypo tube 20B, as shown by arrows 44A and 44B. To prevent hypo tube from sliding when the piezoelectric disk is vibrating, an adhesive may be used to further anchor the hypo tube to the disk.

Figure 7:
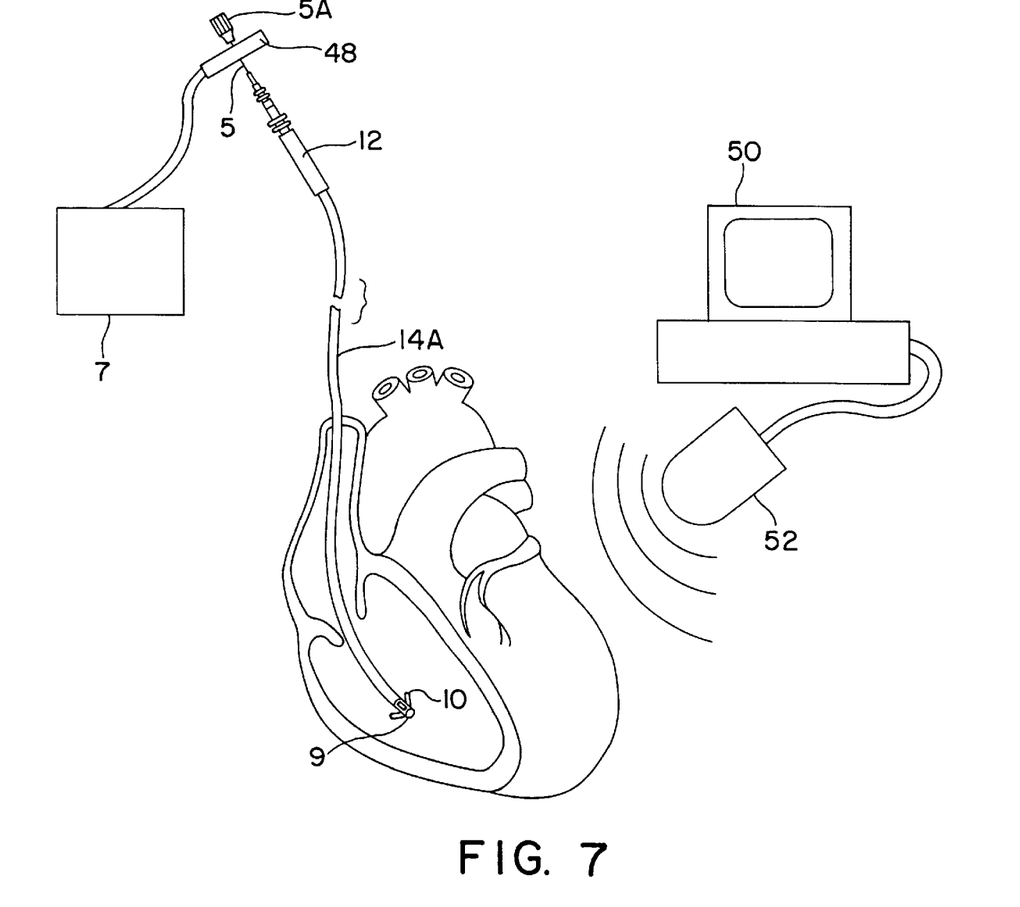
FIG. 7 illustrates the method of using a lead in which the present invention is practiced, using a vibrating stylet and lead in conjunction with an ultrasound scanner.

FIG. 7 illustrates the method of use of leads and catheters according to the present invention. The lead body 11 is advanced through the vascular system into the ventricle by means of stylet 5, shown extending from connector assembly 12 and stylet knob 5A. When activated by the source of ultrasound energy 7, the piezoelectric vibrator 48 causes stylet 5 to vibrate. These vibrations are transferred to the lead body 11 and lead tip and fixation tines 10. As the lead electrode and tines pass through the ultrasound scan of the ultrasound scanner 52, they are rendered visible on the ultrasound display 50.

What is claimed is:

1. An ultrasound imaging system for visualization of a medical device within a body, comprising:
   an elongated tubular member having a curved portion;
   a vibration device, coupled to the elongated tubular member, generating vibrations and transferring the vibrations to the elongated tubular member;
   a guiding device frictionally contacting the elongated tubular member along the curved portion, the elongated tubular member transferring the vibrations to the guiding device; and
   an imaging device detecting the vibrations and producing an image of the medical device using the detected vibrations.

2. The system of claim 1, wherein the curved portion extends from a first curved end to a second curved end, the guiding device continuously receiving the vibrations from the elongated tubular member through one of the first curved end and the second curved end.

3. The system of claim 1, further comprising:
   a first guide guiding insertion of the guiding device whithin the vibration device through the elongated tubular member; and
   a second guide guiding the guiding device outward from the vibration device and with the medical device.

4. The system of claim 3, wherein the first guide is fixedly engaged with the vibration device via a bonding agent and the elongated tubular member slidably engages the bonding agent so that a portion of the elongated tubular member contacting the bonding agent vibrates longitudally.

5. The system of claim 1, wherein the vibration device transfers variations of selectably varying frequencies to the elongated tubular member.

6. The system of claim 1, wherein the elongated tubular member is a hypodermic tube.

7. The system of claim 1, wherein the vibration device further comprises:
   a diaphragm;
   a piezoelectric activator coupled to the diaphragm generating and transferring the vibrations to the diaphragm; and
   a source of ultrasound energy coupled to the piezoelectric activator activating the piezoelectric activator to generate the vibrations.

8. The system of claim 7, wherein the piezoelectric activator is a unimorph piezoelectric disk.

9. The system of claim 7, wherein the piezoelectric activator includes an aperture positioning the elongated tubular member within the vibration device.

10. The system of claim 9, wherein the elongated tubular member is fixedly engaged with the piezoelectric activator along the aperture.

11. The system of claim 1, wherein the guiding device is a stylet.

12. The system of claim 1, wherein the guiding device is a guidewire.

13. The system of claim 1, wherein the medical device is a lead.

14. The system of claim 1, wherein the medical device is a catheter.

15. An ultrasound imaging system of visualization of a medical device within a body, comprising:
   an elongated tubular member having a curved portion;
   a vibration device, coupled to the elongated tubular member, generating vibrations and transferring the vibrations to the elongated tubular member;
   a guiding device frictionally contacting the elongated tubular member, the elongated tubular member transferring the vibrations to the guiding device;
   a first guide guiding insertion of the guiding device within the vibration device through the elongated tubular member;
   a second guide guiding the guiding device outward from the vibration device and within the medical device; and
   an imaging device detecting the vibrations and producing an image of the medical device using the detected vibrations, wherein the elongated tubular member includes a curved portion extending from a first curved end to a second curved end, the guiding device continuously receiving the vibrations from the elongated tubular member through one of the first curved end and the second curved end.

16. The system of claim 15, wherein the first guide is fixedly engaged with the vibration device via a bonding agent and the elongated tubular member slidably engages the bonding agent so the a portion of the elongated tubular member contacting the bonding agent vibrates longitudally.

17. The system of claim 16, wherein the vibration device transfers vibrations of selectably varying frequencies to the elongated tubular member.

18. The system of claim 17, wherein the elongated tubular member is a hypodermic tube.

19. The system of claim 18, wherein the vibration device further comprises:
   a diaphragm;
   a piezoelectric activator coupled to the diaphragm generating and transferring the vibrations to the diaphragm; and
   a source of ultrasound energy coupled to the piezoelectric activator activating the piezoelectric activator to generate the vibrations.

20. The system of claim 19, wherein the piezoelectric activator is a unimorph piezoelectric disk.

21. The system of claim 19, wherein the piezoelectric activator includes an aperture positioning the elongated tubular member within the vibration device.

22. The system of claim 21, wherein the elongated tubular member is fixedly engaged with the piezoelectric activator along the aperture.

23. The system of claim 15, wherein the guiding device is a stylet.

24. The system of claim 15, wherein the guiding device is a guidewire.

25. The system of claim 15, wherein the medical device is a lead.

26. The system of claim 15, wherein the medical device is a catheter.

27. A vibration device generating vibrations utilized during generation of an image corresponding to a medical device being positioned within a patient using a guiding device inserted within the medical device, the vibration device comprising:
   an elongated tubular member, positioned within the vibration device receiving the guiding device as the guiding device is inserted within the medical device through the vibration device, the elongated tubular member having a curved portion frictionally contacting the guiding device and transferring the vibrations to the guiding device through the frictional contact;
   a first guide guiding insertion of the guiding device within the vibration device through the elongated tubular member; and
   a second guide guiding the guiding device outward from the vibration device and within the medical device.

28. The vibration device of claim 27, wherein the first guide is fixedly engaged with the vibration device via a bonding agent and the elongated tubular member slidably engages the bonding agent so that a portion of the elongated tubular member contacting the bonding agent vibrates longitudinally.

29. The vibration device of claim 27, wherein the vibration device transfers vibrations of selectably varying frequencies to the elongated tubular member.

30. The vibration device of claim 27, wherein the elongated tubular member is a hypodermic tube.

31. The vibration device of claim 27, further comprising:
   a diaphragm; and
   a piezoelectric activator coupled to the diaphragm generating and transferring the vibrations to the diaphragm.

32. The vibration device of claim 31, wherein the piezoelectric activator is a unimorph piezoelectric disk.

33. The vibration device of claim 31, wherein the piezoelectric activator includes an aperture positioning the elongated tubular member within the vibration device.

34. The vibration device of claim 33, wherein the elongated tubular member is fixedly engaged with the piezoelectric activator along the aperture.

35. The vibration device of claim 27, wherein the guiding device is a stylet.

36. The vibration device of claim 27, wherein the guiding device is a guidewire.

37. The vibration device of claim 27, wherein the medical device is a lead.

38. The vibration device of claim 27, wherein the medical device is a catheter.

39. A method of visualizing a medical device within a body, comprising the steps of:
   inserting a guiding device within the medical device through an elongated tubular member positioned within a vibration device;
   transferring vibrations from the vibration device to the guiding device through a curved portion of the elongated tubular member;
   transferring the vibrations from the guiding device to the medical device; and
   detecting the vibrations transferred to the medical device and thereby producing an image of the medical device.

40. The method of claim 39 wherein the step of transferring vibrations from the vibration device to the guiding device further comprises the step of selectively varying the transferred vibrations.

* * * * *

UNITED STATES PATENT AND TRADEMARK OFFICE
CERTIFICATE OF CORRECTION

PATENT NO.    : 6,520,916 B1
DATED         : February 18, 2003
INVENTOR(S)   : Kenneth R. Brennen It is certified that error appears in the above-identified patent and that said Letters Patent is hereby corrected as shown below:

Column 6,
Line 2, "device and with the" should read -- device and within the --
Line 37, "system of" should read -- system for --

Signed and Sealed this

Eighteenth Day of May, 2004

JON W. DUDAS
*Acting Director of the United States Patent and Trademark Office*